US012233186B2

(12) United States Patent
Bandyopadhyay et al.

(10) Patent No.: US 12,233,186 B2
(45) Date of Patent: Feb. 25, 2025

(54) FLUOROPOLYMER BASED ANTI-THROMBOTIC COATINGS

(71) Applicant: CERULEAN SCIENTIFIC INC., Durham, NC (US)

(72) Inventors: Saibal Bandyopadhyay, Lancaster, PA (US); Andrew K. Jones, Lancaster, PA (US)

(73) Assignee: Cerulean Scientific Inc., Durham, NC (US)

( * ) Notice: Subject to any disclaimer, the term of this patent is extended or adjusted under 35 U.S.C. 154(b) by 905 days.

(21) Appl. No.: 17/228,414

(22) Filed: Apr. 12, 2021

(65) Prior Publication Data

US 2021/0369921 A1 Dec. 2, 2021

Related U.S. Application Data

(63) Continuation of application No. PCT/US2019/055742, filed on Oct. 10, 2019.

(60) Provisional application No. 62/744,203, filed on Oct. 11, 2018.

(51) Int. Cl.
*A61L 29/08* (2006.01)
*A61M 25/00* (2006.01)
*C08L 27/18* (2006.01)

(52) U.S. Cl.
CPC ....... *A61L 29/085* (2013.01); *A61M 25/0009* (2013.01)

(58) Field of Classification Search
CPC .......... C08L 27/12; C08L 27/18; C08L 27/20; A61L 29/085
See application file for complete search history.

(56) References Cited

U.S. PATENT DOCUMENTS

| 3,068,187 A | 12/1962 | Bolstad et al. |
| 3,274,007 A | 9/1966 | Jones |
| 3,834,544 A | 9/1974 | Tyson, Jr. et al. |
| 3,927,981 A | 12/1975 | Viannay et al. |
| 4,386,170 A | 5/1983 | Monroe |
| 4,633,004 A | 12/1986 | Boutvin et al. |
| 4,787,991 A | 11/1988 | Morozumi et al. |
| 4,861,511 A | 8/1989 | Kaplan |

(Continued)

FOREIGN PATENT DOCUMENTS

| CN | 1360618 A | 7/2002 |
| CN | 1884398 A | 12/2006 |

(Continued)

OTHER PUBLICATIONS

Israelachvili, "Intermolecular and Surface Forces—Third Edition," Academic Press, 706 pages (No Month Listed 2011).

(Continued)

*Primary Examiner* — Catherine S Branch
(74) *Attorney, Agent, or Firm* — Meunier Carlin & Curfman LLC (57) ABSTRACT

The present disclosure provides for medical devices comprising one or more components comprised of a fluoropolymer and/or perfluorinated polymer and a liquid comprised of one or more fluorinated and/or perfluorinated liquids, wherein at least a portion of a surface of the one or more components comprised of a fluoropolymer and/or perfluorinated polymer comprises a surface layer of the fluorinated and/or perfluorinated liquid.

21 Claims, 4 Drawing Sheets

(56) References Cited

U.S. PATENT DOCUMENTS

| | | |
|---|---|---|
| 4,937,596 A | 6/1990 | Schmid |
| 5,091,205 A | 2/1992 | Fan |
| 5,178,267 A | 1/1993 | Grabenkort et al. |
| 5,246,109 A | 9/1993 | Marke et al. |
| 5,264,131 A | 11/1993 | Ishida et al. |
| 5,277,176 A | 1/1994 | Habashi et al. |
| 5,358,719 A | 10/1994 | Mellul et al. |
| 5,372,888 A | 12/1994 | Ogawa et al. |
| 5,425,989 A | 6/1995 | Ogawa et al. |
| 5,429,184 A | 7/1995 | Bach et al. |
| 5,578,340 A | 11/1996 | Ogawa |
| 5,602,214 A | 2/1997 | Lin et al. |
| 5,620,778 A | 4/1997 | Clatworthy |
| 5,624,713 A | 4/1997 | Ramer |
| 5,630,846 A | 5/1997 | Hara et al. |
| 5,736,251 A | 4/1998 | Pinchuk et al. |
| 5,798,409 A | 8/1998 | Ho |
| 5,804,318 A | 9/1998 | Pinchuk et al. |
| 6,071,981 A | 6/2000 | Johnson et al. |
| 6,171,673 B1 | 1/2001 | Tanaka et al. |
| 6,232,379 B1 | 5/2001 | Takita |
| 6,247,603 B1 | 6/2001 | Farrell et al. |
| 6,447,919 B1 | 9/2002 | Brown et al. |
| 6,511,753 B1 | 1/2003 | Teranishi et al. |
| 6,830,149 B2 | 12/2004 | Merboth et al. |
| 6,889,839 B1 | 5/2005 | Rosten et al. |
| 7,189,934 B2 | 3/2007 | Youngner |
| 7,192,993 B1 | 3/2007 | Sarangapani et al. |
| 7,431,989 B2 | 10/2008 | Sakhrani et al. |
| 7,560,492 B1 | 7/2009 | Claude et al. |
| 7,666,514 B2 | 2/2010 | Sakamoto et al. |
| 7,723,405 B2 | 5/2010 | Braun et al. |
| 7,811,666 B2 | 10/2010 | Dry |
| 7,877,968 B2 | 2/2011 | Kim et al. |
| 9,121,306 B2 | 9/2015 | Aizenberg et al. |
| 9,121,307 B2 | 9/2015 | Aizenberg et al. |
| 9,265,578 B2 | 2/2016 | Dacey |
| 9,353,646 B2 | 5/2016 | Aizenberg et al. |
| 9,630,224 B2 | 4/2017 | Aizenberg et al. |
| 9,932,484 B2 | 4/2018 | Aizenberg et al. |
| 9,932,482 B2 | 5/2018 | Aizenberg et al. |
| 10,011,800 B2 | 7/2018 | Aizenberg et al. |
| 10,233,334 B2 | 3/2019 | Aizenberg et al. |
| 10,550,272 B2 | 2/2020 | Aizenberg et al. |
| 10,982,100 B2 | 4/2021 | Aizenberg et al. |
| 11,118,067 B2 | 9/2021 | Aizenberg et al. |
| 2001/0014711 A1 | 8/2001 | Levy |
| 2003/0212232 A1 | 11/2003 | Majeti et al. |
| 2004/0034941 A1 | 2/2004 | Iwato et al. |
| 2004/0186211 A1 | 9/2004 | Howell et al. |
| 2005/0003146 A1 | 1/2005 | Spath |
| 2005/0164008 A1 | 7/2005 | Rukavina |
| 2006/0024504 A1 | 2/2006 | Nelson et al. |
| 2006/0153993 A1 | 7/2006 | Schmidt et al. |
| 2006/0159645 A1 | 7/2006 | Miller et al. |
| 2006/0194008 A1 | 8/2006 | Schwartz et al. |
| 2006/0204645 A1 | 9/2006 | Godfried |
| 2006/0211802 A1 | 9/2006 | Asgari |
| 2007/0039832 A1 | 2/2007 | Heikenfeld |
| 2007/0141306 A1 | 6/2007 | Kasai et al. |
| 2007/0154626 A1 | 7/2007 | Sasaki et al. |
| 2007/0166344 A1 | 7/2007 | Qu et al. |
| 2007/0184733 A1 | 8/2007 | Manley et al. |
| 2007/0224391 A1 | 9/2007 | Krupenkin et al. |
| 2007/0254000 A1 | 11/2007 | Guo et al. |
| 2008/0118763 A1 | 5/2008 | Balow et al. |
| 2008/0195170 A1 | 8/2008 | Asgari |
| 2009/0078153 A1 | 3/2009 | Shchukin et al. |
| 2009/0098299 A1 | 4/2009 | Cheng |
| 2009/0209922 A1 | 8/2009 | Boisjoly |
| 2010/0009583 A1 | 1/2010 | Bringley et al. |
| 2010/0021748 A1 | 1/2010 | Hu et al. |
| 2010/0135852 A1 | 6/2010 | Kawakatsu et al. |
| 2010/0145286 A1 | 6/2010 | Zhang |
| 2010/0210745 A1 | 8/2010 | McDaniel et al. |
| 2010/0285084 A1 | 11/2010 | Yang et al. |
| 2011/0136653 A1 | 6/2011 | Koebel et al. |
| 2011/0165206 A1 | 7/2011 | Liu et al. |
| 2011/0203688 A1 | 8/2011 | Reed et al. |
| 2011/0283778 A1 | 11/2011 | Angelescu et al. |
| 2011/0287987 A1 | 11/2011 | Mordukhovich et al. |
| 2011/0305881 A1 | 12/2011 | Schultz et al. |
| 2012/0004357 A1 | 1/2012 | Roulleaux et al. |
| 2012/0052241 A1 | 3/2012 | King et al. |
| 2012/0141052 A1 | 6/2012 | Drew et al. |
| 2012/0172787 A1 | 7/2012 | McClain et al. |
| 2013/0032316 A1 | 2/2013 | Dhiman et al. |
| 2013/0110222 A1 | 5/2013 | Slager |
| 2014/0187666 A1 | 7/2014 | Aizenberg et al. |
| 2014/0342954 A1 | 11/2014 | Ingber et al. |
| 2015/0209198 A1 | 7/2015 | Aizenberg et al. |
| 2015/0209846 A1 | 7/2015 | Aizenberg et al. |
| 2015/0210951 A1 | 7/2015 | Aizenberg et al. |
| 2016/0144079 A1 | 5/2016 | Ingber et al. |
| 2016/0288062 A1 | 10/2016 | Ait-Haddou et al. |
| 2017/0367705 A1 | 12/2017 | Alston et al. |
| 2018/0362875 A1 | 12/2018 | Aizenberg et al. |
| 2021/0023292 A1 | 1/2021 | Bandyopadhyay et al. |
| 2021/0369379 A1 | 12/2021 | Bandyopadhyay et al. |

FOREIGN PATENT DOCUMENTS

| | | | |
|---|---|---|---|
| CN | 101052667 A | 10/2007 | |
| CN | 101198542 A | 6/2008 | |
| CN | 101374607 A | 2/2009 | |
| CN | 101444777 A | 6/2009 | |
| CN | 101538395 A | 9/2009 | |
| CN | 101580753 A | 11/2009 | |
| CN | 101675156 A | 3/2010 | |
| CN | 101918621 A | 12/2010 | |
| CN | 102388180 A | 3/2012 | |
| DE | 19818956 A1 | 11/1998 | |
| EP | 0166998 A2 | 1/1986 | |
| EP | 0338418 A1 | 10/1989 | |
| EP | 0497204 A2 | 8/1992 | |
| EP | 0893164 A2 | 1/1999 | |
| EP | 1002825 A2 | 5/2000 | |
| EP | 1487590 B1 | 5/2006 | |
| EP | 2228053 A1 | 9/2010 | |
| EP | 2363438 A1 | 9/2011 | |
| EP | 3263167 A1 * | 1/2018 | ........... A61L 29/041 |
| FR | 2943066 A1 | 9/2010 | |
| JP | S60-259269 A | 12/1985 | |
| JP | 62-063219 A | 3/1987 | |
| JP | S62-252477 A | 11/1987 | |
| JP | 01-170932 A | 7/1989 | |
| JP | 04-270649 A | 9/1992 | |
| JP | 05-229402 A | 9/1993 | |
| JP | 5240251 B2 | 9/1993 | |
| JP | H06-180882 A | 6/1994 | |
| JP | H06-48685 U | 7/1994 | |
| JP | 07-242769 A | 9/1995 | |
| JP | H08-12816 A | 1/1996 | |
| JP | H10-183049 A | 7/1998 | |
| JP | H11-64772 A | 3/1999 | |
| JP | H11-345441 A | 12/1999 | |
| JP | 2000-510353 A | 8/2000 | |
| JP | 2001-131413 A | 5/2001 | |
| JP | 2003-170540 A | 6/2003 | |
| JP | 2004-037764 A | 2/2004 | |
| JP | 2004-136630 A | 5/2004 | |
| JP | 2005-082848 A | 3/2005 | |
| JP | 2005-231084 A | 9/2005 | |
| JP | 2006-280843 A | 10/2006 | |
| JP | 2008-223003 A | 9/2008 | |
| JP | 2009-523890 A | 6/2009 | |
| JP | 2010-047890 A | 3/2010 | |
| JP | 2010-167929 A | 8/2010 | |
| JP | 6228012 B2 | 11/2017 | |
| KR | 2009-0026199 A | 3/2009 | |
| WO | 92/10532 A1 | 6/1992 | |
| WO | 93/17077 A1 | 9/1993 | |
| WO | 99/36490 A1 | 7/1999 | |
| WO | 01/78800 A1 | 10/2001 | |

(56) References Cited

FOREIGN PATENT DOCUMENTS

| | | |
|---|---|---|
| WO | 02/09647 A2 | 2/2002 |
| WO | 03/013827 A1 | 2/2003 |
| WO | 2005/091309 A1 | 9/2005 |
| WO | 2005/121288 A1 | 12/2005 |
| WO | 2006/091235 A1 | 8/2006 |
| WO | 2006/118460 A1 | 11/2006 |
| WO | 2007/130734 A2 | 11/2007 |
| WO | 2008/013825 A2 | 1/2008 |
| WO | 2008/017472 A1 | 2/2008 |
| WO | 2008/049108 A1 | 4/2008 |
| WO | 2008/120505 A1 | 10/2008 |
| WO | 2010/028752 A1 | 3/2010 |
| WO | 2010/042804 A2 | 4/2010 |
| WO | 2010/065960 A2 | 6/2010 |
| WO | 2010/116045 A1 | 10/2010 |
| WO | 2011/005200 A1 | 1/2011 |
| WO | 2011/049896 A2 | 4/2011 |
| WO | 2012009238 A2 | 1/2012 |
| WO | 2012/055821 A1 | 5/2012 |
| WO | 2012/055825 A1 | 5/2012 |
| WO | 2012/100099 A2 | 7/2012 |
| WO | 2012/100100 A2 | 7/2012 |
| WO | 2013/022467 A2 | 2/2013 |
| WO | 2013/106588 A1 | 7/2013 |
| WO | 2013/115868 A2 | 8/2013 |
| WO | 2014012039 A1 | 1/2014 |
| WO | 2014012052 A1 | 1/2014 |
| WO | 2014012072 A2 | 1/2014 |
| WO | 2014012078 A2 | 1/2014 |
| WO | 2014012079 A1 | 1/2014 |
| WO | WO-2017189855 A1 * | 11/2017 ......... A61B 1/00066 |

OTHER PUBLICATIONS

Karchmer et al., "*Staphylococcus epidermidis* causing prosthetic valve endocarditis: microbiologic and clinical observations as guides to therapy," Ann Intern Med, vol. 98, pp. 447-455 (Apr. 1, 1983).
Keck et al., "Preparation of partially fluorinated aryl/alkyl vinylene ether polymers," Polymer International, vol. 62, Issue 10, pp. 1485-1491, Oct. 2013.
Khoo et al., "Directed assembly of PEGylated-peptide coatings for infection-resistant titanium metal," J. Am. Chem. Soc., vol. 131, pp. 10992-10997 (Jul. 21, 2009).
Kim et al., "Structural Transformation by Electrodeposition on Patterned Substrates (STEPS): A new Versatile Nano-fabrication Method," Nano Letters, vol. 12, No. 2, pp. A-G (Mar. 2011).
Kobayashi et al., "Surface tension of poly[(3,3,4,4,5,5,6,6,6-nanoflurohexyl methlisiloxane]," Macromolecules, 1990, vol. 23, No. 23, pp. 4929-4933.
Koschwanez et al., "In vitro and in vivo characterization of porous poly-L-lactic acid coatings for subcutaneously implanted glucose sensors," Journal of Biomedical Materials Research Part A, pp. 792-807 (Dec. 2008).
Lee et al., "Fast fabrication of long-range ordered porous alumina membranes by hard anodization," Nature Mater, vol. 5, pp. 741-747 (Sep. 2006).
Vogel et al., "A Convenient Method to Produce Close- and Non-close-Packed Monolayers using Direct Assembly at the Air-Water Interface and Subsequent Plasma-Induced Size Reduction," Macromolecular Chemistry and Physics, vol. 212, pp. 1719-1734 (2011).
Li et al., "Bioinspired Self-Healing Superhydrophobic Coatings," Angewandte Chemie, vol. 49, No. 35, pp. 6129-6133 (Aug. 16, 2010).
Lillehoj et al., "A self-pumping lab-on-a-chip for rapid detection of botulinium toxin," Lab Chips, vol. 10, pp. 2265-2270 (Jun. 11, 2010).
Lin et al., "Surface modification of polytetrafluoroethylene films by plasma pretreatment and graft copolymierization to improve their adhesion to bismaleimide," Polym. Int., vol. 58, No. 1, pp. 46-53 (Jan. 2009).

Liu et al., "Organogel-based Thin Films for Self-Cleaning on Various Surfaces," Advanced Materials, 5 pages, (2013).
Matsunaga, et al., "Controlling the Stability and Reversibility of Micropillar Assembly by Surface Chemistry," J. Am. Chem. Soc., vol. 133, No. 14, pp. 5545-5553, 4 pages (Dec. 2, 2011).
Meuler et al., "Relationships between Water Wettability and Ice Adhesion," ACS Applied Materials and Interfaces, vol. 2, No. 11, 31 pages (Oct. 15, 2010).
Microsurfaces, Inc., "Anti-Stiction Coatings in MEMS Devices," MicroSurfaces, Inc., retrieved from website URL: http://memsurface.com/stiction.html, 2 pages (retrieved on Dec. 8, 2011).
Miller-Chou et al., "A review of polymer dissolution," Progress in Polymer Science, vol. 28, pp. 1223-1270, (2003).
Mori, "Silicone Surface Treatment," Journal of the Society of Rubber Industry of Japan (Nippon Gomu Kyokaishi), 1986, vol. 59, Issue 11, pp. 627-633. ISSN: 0029-022X. Released Jul. 9, 2007. Full English translation with original. (<https://www.jstage.jst.go.jp/article/gomu1944/59/11/59 11 627/ article/-char/en>).
Munro et al., "Deterioration of pH electrode response due to biofilm formation on the glass membrane," Sensor Actuat B-Chem, vol. 37, pp. 187-194 (Dec. 1996).
Nakao, "Silicone Water Repellents," Journal of Synthetic Organic Chemistry, Japan, Jul. 1966, vol. 24, No. 7, pp. 598-608. Full English translation with original. ISSN 0037-9980. (<https://www.istaae.ist.ao.io/article/vukiaoseikvokaishi 1943/24/7 /24 7 598/ article/-char/en>).
Nguyen, "Quantitative Testing of Robustness on Superomniphobic Surfaces by Drop Impact", Langmuir, 26 (23):18369-18373, Dec. 7, 2010.
Niimi et al., "The effects of heparin coating of oxygenator fibers on platelet adhesion and protein adsorption," Anesth. Analg., 1999, vol. 89, pp. 573-579.
Noetzel et al., "Shunt fluid examination: risks and benefits in the evaluation of shunt malfunction and infection," J. Neurosurg., vol. 61, pp. 328-332 (Aug. 1984).
Nosonovsky et al., "Biomimetic Superhydrophobic Surfaces: Multiscale Approach", Nano Lett, 7(9):2633-2637, Aug. 17, 2007.
Nosonovsky, "Multiscale Roughness and Stability of Superhydrophobic Biomimetic Interfaces", Lanamuir, 23(6):3157-3161, Feb. 13, 2007.
O'Toole et al., "Biofilm Formation as Microbial Development," Annu. Rev. Microbiol., 2000, vol. 54, pp. 49-79.
Park et al., "Bacterial adhesion on PEG modified polyurethane surfaces," Biomaterials, vol. 19, No. 7-9, pp. 851-859 (Apr.-May 1998).
Poetes et al., "Metastable Underwater Superhydrophobicity," Physical Review Letters, vol. 105, Issue 16, pp. 166104.1-166104.4 Published (Oct. 14, 2010).
Pokroy et al., "Fabrication of Bio-Inspired Actuated Nanostructures with Arbitrary Geometry and Stiffness," Adv. Mater, vol. 21, pp. 463-469 (Jan. 26, 2009).
Prakash et al., "Microfluidic Bubble Logic," Science, vol. 315, No. 5813, pp. 832-835 (Sep. 2008).
Prime et al., "Self-assembled organic monolayers: model systems for studying adsorption of proteins at surfaces," Science, vol. 252, No. 5009, p. 1164-1167 (May 24, 1991).
Quere, "Wetting and roughness," Annu. Rev. Mater. Res., vol. 38, pp. 71-99 (Apr. 7, 2008).
Raza et al., "Superhydrophobic Surfaces by Anomalous Fluoroalkylsilane Self-Assembly on Silica Nanosphere Arrays", Langmuir, 26(15):12962-12972, Aug. 3, 2010.
Vogel et al., "From soft to hard: the generation of functional and complex colloidal monolayers for nanolithography," Soft Matter, vol. 8, pp. 4044-4061 (2012).
Rothemund, "Folding DNA to create nanoscale shapes and patterns," Nature, vol. 440, pp. 297-302, Mar. 16, 2006.
Rowe, "Chemistry and Technology of Flavors and Fragrances," Blackwell Publishing Ltd, 12 pages—Title Page, Copyright Page and Table of Contents Only (2005).
Saido et al., "A Growth of Aspergillus Niger on Surface of Polymer Films was Observed by FT-IR and Scanning Electron Microscope", Materials Life, Oct. 8, 1991, vol. 3 No. 4, pp. 218-224. English translation.

(56) References Cited

OTHER PUBLICATIONS

Shaffer et al., "Liquid Ventilation," Pediatric Pulmonology, vol. 14, pp. 102-109 (Oct. 1992).
Tuteja et al., "Designing Superoleophobic Surfaces," Science, vol. 318, No. 5856, pp. 1618-1622 (Dec. 7, 2007).
Shafrin et al., "Constitutive relations in the wetting of low energy surfaces and the theory of the retraction method of preparing monolayers," J. Phys. Chem., vol. 64, pp. 519-524 (May 1960).
Shi et al., "Microstructure and friction properties of PVA/PVP hydrogels for articular cartilage repair as function of polymerization degree and polymer concentration," Wear, Jul. 30, 2013, vol. 305, pp. 280-285.
Skattum et al., "Complement deficiency states and associated infections," Mol. Immunol, vol. 48, No. 14, pp. 1643-1655 (Aug. 2011).
Sohail et al., "Risk factor analysis of permanent pacemaker infection," Clin Infect Dis, vol. 45, pp. 166-173 (Jul. 15, 2007).
Stober et al., "Controlled growth of monodisperse silica spheres in the micron size range," Journal of Colloid and Interface Science, vol. 26, No. 1, pp. 62-69 (Jan. 1968).
Trevors, "Silver resistance and accumulation in bacteria," Enzyme and Mircobial Technology, vol. 9, No. 6, pp. 331-333 (Jun. 1987).
Tuli et al., "Risk factors for repeated cerebrospinal shunt failures in pediatric patients with hydrocephalus," J. Neurosurg., vol. 92, pp. 31-38 (Jan. 2000).
Tuteja et al., "Robust omniphobic surfaces," PNAS, vol. 105, No. 47, pp. 18200-18205 (Nov. 25, 2008).
Varanasi et al., "Frost formation and ice adhesion on superhydrophobic surfaces," Applied Physics Letters, 2010, vol. 97, pp. 234102-1-234102-3.
International Search Report and Written Opinion dated Dec. 13, 2019, for International Application No. PCT/US2019/055743.
International Search Report and Written Opinion dated May 14, 2019, for International Application No. PCT/US2019/012580.
Abbott et al., "Mass Production of Bio-Inspired Structured Surfaces", Proceedings of the Institution of Mechanical Engineers, Part C: Journal of Mechanical Engineering Science, 221(10):1181-1191, Oct. 1, 2007.
Afessa et al., "Association Between a Silver-Coated Endotracheal Tube and Reduced Mortality in Patients With Ventilator-Associated Pneumonia," Chest, vol. 137, pp. 1015-1021 (May 2010).
Ahuja et al., "Nanonails: A Simple Geometrical Approach to Electrically Tunable Superlyophobic Surfaces," Langmuir, 2008, vol. 24, pp. 9-14.
Akamatsu, "Water-repellent Coating on Glass," New Glass, Sep. 2006, vol. 21, No. 3, pp. 27-34. Full English translation with original. ISSN 0914-6563. (<https://www.newglass.jp/mag/TITL/maghtml/82e.html>).
Badrossamay et al., "Nanofiber Assembly by Rotary Jet-Spinning," Nano Letters, vol. 10, No. 6, pp. 2257-2261, 11 pages (Jun. 9, 2010).
Bai et al., "Core-Annular Flows," Annual Review Fluid Mechanics, vol. 29, pp. 65-90 (Jan. 1997).
Banerjee et al., "Antifouling coatings: recent developments in the design of surfaces that prevent fouling by proteins, bacteria, and marine organisms," Advanced Materials, 2011, 23, pp. 690-718.
Banerjee et al., "Infection control during GI endoscopy," Gastrointest Endosc, vol. 67, pp. 781-790 (May 2008).
Banhart, "Manufacture, characterisation and application of cellular metals and metal forms," Progress in Materials Science, 2001, vol. 46, pp. 559-632.
Barstad et al., "Monocyte procoagulant activity induced by adherence to an artificial surface is reduced by end-point immobilized heparin-coating of the surface", Thrombosis and haemostatis, 1997, vol. 79, pp. 302-305.
Barthlott et al., "Purity of the sacred lotus, or escape from contamination in biological surfaces," Planta, 1997, vol. 202, pp. 1-8.
Bauer et al., "The Insect-Trapping Rim of Nepenthes Pitchers", Plant Signaling & Behavior, 4(11):1019-1023, Nov. 1, 2009.

Beely et al., "Electron Microscopy as a Tool for Assessment of Anticoagulation Strategies During Extracorporeal Life Support: The Proof Is on the Membrane," ASAIO Journal, vol. 62(5), pp. 525-532 (Oct. 2016).
Beilenhoff et al., "ESGE-ESGENA guideline: Cleaning and disinfection in gastrointestinal endoscopy Update 2008," Endoscopy, 2008, vol. 40, pp. 939-957.
Berger, R. G., "Flavours and Fragrances: Chemistry, Bioprocessing and Sustainability," Springer, 15 pages—Title Page, Copyright Page and Table of Contents Only (Feb. 14, 2007).
Bhardwaj et al., "A review of the development of a vehicle for localized and controlled drug delivery for implantable biosensors," J. Diabetes Sci Technol., vol. 2, pp. 1016-1029 (Nov. 2008).
Bico et al., "Rough wetting," Europhysics Letters, vol. 55, No. 2, pp. 214-220 (Jul. 15, 2001).
Bico et al., "Wetting of textured surfaces," Colloids and Surfaces, A: Physicochemical and Engineering Aspects, 2002, vol. 206, pp. 41-46.
Bocquet et al., "A smooth future?," Nature Mater, vol. 10, pp. 334-337 (May 2011).
Bohn et al., "Insect Aquaplaning: Nepenthes Pitcher Plants Capture Prey with the Peristome, a Fully Wettable Water-Lubricated Anisotropic Surface", PNAS, 101 (39):14138-14143, Sep. 21, 2008.
Bos et al., "Retention of bacteria on a substratum surface with micro patterned hydrophobicity," Fems Microbiology Letters, vol. 189, No. 2, pp. 311-315 (Aug. 15, 2000).
Cassie et al., "Wettability of Porous Surfaces", Transactions of the Faraday Society, 1944, vol. 40, pp. 546-551.
Cassie et al.," Large contact angles of plant and animal surfaces," Nature, vol. 155, pp. 21-22, Jan. 6, 1945.
Chaudhury et al., "Direct Measurement of Interfacial Interactions between Semispherical Lenses and Flat Sheets of Poly (dimethysiloxane) and Their Chemical Derivatives," Langmuir, 1991, vol. 7, pp. 1013-1025.
Chen et al., "Surface hydration: Principles and applications toward low-fouling/nonfouling biomaterials," Polymer, vol. 51, pp. 5283-5293 (Aug. 10, 2010).
Clark, Jr. et al., "Survival of Mammals Breathing Organic Liquid Equilibriated With Oxygen at Atmospheric Pressure", Science, vol. 152, pp. 1755-1756 (Jun. 24, 1966).
Costerton et al., "Bacterial biofilms in nature and disease," Ann. Rev. Microbiol, 1987, vol. 41, pp. 435-464.
Costerton et al., "Bacterial biofilms: a common cause of persistent infections," Science, vol. 284, No. 5418, pp. 1318-1322 (May 21, 1999).
Cribier et al., "Percutaneous transcatheter implantation of an aortic valve prothesis for calcific aortic stenosis—First human case description," Circulation, vol. 106, pp. 3006-3008 (Nov. 25, 2002).
Crnich et al., "The Promise of Novel Technology for the Prevention of Intravascular Device-Related Bloodstream Infection. I. Pathogenesis and Short-Term Devices," Clinical Infectious Diseases, vol. 34, pp. 1232-1242 (May 1, 2002).
Database WPI Weekly 198933, Thomson Scientific, London, GB, XP-002694116; AN 1989-237086 & JP1170932A (Nippon Sheet Glass Co. Ltd.) 1 page (Jul. 6, 1989) (abstract).
De Beer et al., "Microbial Biofilms," Prokaryotes, 2006, vol. 1, pp. 904-937.
De Gennes et al., "Capillarity and Wetting Phenomena: drops, bubbles, pearls, waves," Springer, New York, 2004.
Dieter, "Coronary artery stent infection," Clin. Cardiol., vol. 23, pp. 808-810 (Jan. 6, 2000).
Dismukes et al., "Prosthetic valve endocarditis. Analysis of 38 cases," Circulation, vol. 48, pp. 365-377 (Aug. 1973).
Drelich et al., "Measurement of Interfacial Tension in Fluid-Fluid Systems", Encyclopedia of Surface and Colloid Science, pp. 3152-3166 (Jan. 2002).
Fadeev et al., "Surface Modification of Poly(ethylene terephthalate) To Prepare Surfaces with Silica-Like Reactivity," Langmuir, vol. 14, No. 19, pp. 5586-5593 (Aug. 21, 1998).
Fowkes, "Attractive forces at interfaces," Ind. Eng. Chem., vol. 56, pp. 40-52 (Dec. 1964).

(56) References Cited

OTHER PUBLICATIONS

Fuerstman, et al., "Coding/Decoding and Reversibility of droplet trains in Microfluidic networks," Science, vol. 315, No. 5813, pp. 828-832 (Feb. 9, 2007).
Gao et al., "Teflon is Hydrophobic Comments on Definitions of Hydrophobic, Shear versus Tensile Hydrophobicity, and Wettability Characterization," Langmuir, vol. 24, pp. 9183-9188 (Sep. 2, 2008).
Garg et al., "Acute Coronary Syndrome Caused by Coronary Artery Mycotic Aneurysm Due to Late Stent Infection Localized With Radiolabeled Autologous Leukocyte Imaging," Clin. Nucl. Med., vol. 34, pp. 753-755 (Nov. 2009).
George et al., Self-assembling polystyrene-block poly(ethylene oxide) copolymer surface coatings: resistance to protein and cell adhesion, Biomaterials, vol. 30 pp. 2449-2456 (May 2009).
Gristina et al., "Biomaterial-centered sepsis and the total artifical heart. Microbial adhesion vs tissue integration," JAMA, vol. 259, pp. 870-874 (Feb. 1988).
Hall-Stoodley et al., "Bacterial biofilms: from the natural environment to infectious diseases," Nature Reviews Microbiology, vol. 2, No. 2, pp. 95-108 (Feb. 2004).
Hatton et al., "Assembly of large-area, highly ordered, crack-free inverse opal films," Proceedings of the National Academy of Science of the United States of America, vol. 107, No. 23, pp. 10354-10359 (Jun. 8, 2010).
Hearn et al., "Endovascular stent infection with delayed bacterial challenge," American Journal of Surgery, vol. 174, pp. 157-159 (Aug. 1997).
Hejazi et al., "Wetting Transitions in Two-, Three-, and Four-Phase Systems", Langmuir, 2B:2173-2180, Nov. 5, 2011.
Hozumi et al., "Hydrophobization of Metal/Metal Oxide Surfaces Using Monolayer Films", Journal of the Surface Finishing Society of Japan, Oct. 9, 2009, vol. 60, No. 1, pp. 16-20. English translation.
Nazaki et al., "Surface modification of poly (tetrafluoroethylene) with ArF excimer laser irradiation," J. Photopoly. Sci. Technol. vol. 7, No. 2, pp. 389-395 (1994).
Shino et al., "Wicking Within Forests of Micropillars", EPL Journal, vol. 79, pp. 56005-p1-56005-p5, Sep. 2007.
International Search Report and Written Opinion, International Application No. PCT/US2019/055742 (published under WO 2020/077160), 13 pages (Jan. 3, 2020).
Leslie et al., "New anticoagulant coatings and hemostasis assessment tools to avoid complications with pediatric left ventricular assist devices," *The Journal of Thoracic and Cardioascular Surgery*, vol. 154, pp. 1364-1366 (May 16, 2017).
Zhu et al., "Ice-phobic Coatings Based on Silicon-Oil-Infused Polydimethylsiloxane," American Chemical Society Applied Materials & Interfaces, vol. 5, pp. 4053-4062, (2013).

Vogel et al., "Wafer-Scale Fabrication of Ordered Binary Colloidal Monolayers with Adjustable Stoichiometries," Advanced Functional Materials, vol. 21, pp. 3064-3073, (2011).
Voskerician et al., "Biocompatibility and biofouling of MEMS drug delivery devices," Biomaterials, vol. 24, pp. 1959-1967 (2003).
Wasserscheid et al., "Ionic Liquids in Synthesis," Wiley-VCH Verlag Gmbh & Co., 380 pages (2002).
Wenzel, "Resistance of Solid Surfaces to Wetting by Water", Industrial and Engineering Chemistry, 28(8):988-994, Aug. 1936, 7 pages.
Williams et al., "Etch Rates for Micromachining Processing—Part II," Journal of Microelectromechanical Systems, vol. 12, No. 6, pp. 761-778 (Dec. 2003).
Wilson et al., "Biosensors for real-time in vivo measurements," Biosens. Bioelectron, vol. 20, pp. 2388-2403 (Jan. 15, 2005).
Wong et al., "Deformation of DNA Molecules by Hydrodynamic Focusing," Journal of Fluid Mechanics, 2003, vol. 497, pp. 55-65.
Wong et al., "Bioinspired Self-Repairing Slippery Surfaces with Pressure-Stable Omniphobicity", Nature, 477 (7365):443-447, Jan. 1, 2011.
Wong et al., "Closed-loop control of cellular functions using combinatory drugs guided by a stochastic search algorithm," Proceedings of National Academy of Science for the United States of America, vol. 105, No. 13, pp. 5105-5110 (Apr. 1, 2008).
Wool, "Self-Healing Materials: A Review", Soft Matter, 4:400-418, Advance Article published on line, Jan. 10, 2008.
Xu et al., "Approaching Zero: Using Fractured Crystals in Metrology for Replica Molding," J. Am. Chem. Soc., 2005, vol. 127, No. 3, pp. 854-855.
Zhao et al., "Antibacterial coatings on titanium implants," Journal of Biomedical Materials Research Part B: Applied Biomaterials, vol. 91, No. 1, pp. 4 70-480 (No Month Listed 2009).
International Search Report and Written Opinion dated Aug. 21, 2012 for PCT/US2012/021929.
International Search Report and Written Opinion dated Jun. 6, 2013, for PCT/US2013/021056.
International Search Report and Written Opinion dated Dec. 4, 2013, for PCT/US2013/050403.
International Search Report and Written Opinion dated Sep. 5, 2013, for PCT/US2013/050364.
International Search Report and Written Opinion dated May 13, 2014, for PCT/US2013/050396.
International Search Report and Written Opinion dated Jun. 4, 2014, for PCT/US2013/050402.
International Search Report and Written Opinion dated Sep. 13, 2013, for PCT/US2013/050343.
International Search Report and Written Opinion dated Aug. 10, 2012, for PCT/US2012/021928.

\* cited by examiner

FLUOROPOLYMER BASED ANTI-THROMBOTIC COATINGS

RELATED APPLICATIONS

This application is a continuation of International Application No. PCT/US2019/055742 filed Oct. 10, 2019, which claims the benefit of U.S. Provisional Application No. 62/744,203 filed Oct. 11, 2018, each of which applications is incorporated herein by reference in its entirety.

BACKGROUND

When devices are inserted in the human body, they tend to induce thrombosis and attract biofilm formation. Both of these events frequently lead to infection and unintended clotting. This invention provides an inert fluorinated coating for medical devices inserted in humans which prevents the formation of biofilms and does not initiate thrombosis.

SUMMARY

The present disclosure provides for medical devices comprising one or more components comprised of a fluoropolymer and/or perfluorinated polymer and a liquid comprised of one or more fluorinated and/or perfluorinated liquids wherein at least a portion of a surface of the one or more components comprised of a fluoropolymer and/or perfluorinated polymer comprises a surface layer of the fluorinated and/or perfluorinated liquid. Medical devices having one or more components comprised of a fluoropolymer and/or perfluorinated polymer and a liquid comprised of one or more fluorinated and/or perfluorinated liquids provided for herein include, but are not limited to, catheters, tubing, shunts, grafts, stents, extracorporeal circuits including extracorporeal membrane oxygenation circuits, implanted devices, medical testing devices, cell culture equipment (e.g., bags, plates and flasks), blood bags, and artificial organs.

The disclosure also provides for methods of making and using such medical devices in, for example, methods of treatment. In an embodiment, the methods of treatment comprise contacting mammalian (e.g., human) blood, plasma, serum, cerebrospinal fluid, and/or a mammalian (e.g., human) body or part thereof with a medical device having one or more components comprised of a fluoropolymer and/or perfluorinated polymer and a liquid comprised of one or more fluorinated and/or perfluorinated liquids.

DETAILED DESCRIPTION

Medical devices made with or coated with certain perfluoropolymer and/or fluoropolymers when lubricated with fluorinated and/or perfluorinated liquids show reduced thrombogenicity, biofilm adhesion, single cell adhesion and immune response. The medical devices may be prepared from a variety of perfluoropolymers and/or fluoropolymers and fluorinated and/or perfluorinated liquids and utilized in a variety of processes including medical treatment of human patients and subjects.

As used herein "fluorinated" with respect to molecules means molecules having fluorine in place of hydrogen. Fluorinated molecules include perfluorinated molecules where all hydrogens have been substituted with a fluorine.

"Fluorinated liquids" as used herein refer to chemical compositions that are liquid at 22° C. and one atmosphere of pressure comprised of, consisting essentially of, or consisting of hydrocarbons, or molecules having a hydrocarbon moiety (e.g., an alkyl group), in which one or more hydrogen atoms bound to a carbon atom have been replaced by a fluorine atom. Fluorinated liquids include perfluorinated liquids where each hydrogen atom has been replaced by a fluorine atom. The term "fluorinated liquid" is understood to include compositions comprising one or more fluorinated liquids and/or perfluorinated liquids unless stated otherwise.

Where both fluorinated liquid and perfluorinated liquid are used (e.g., fluorinated liquid and/or perfluorinated liquid), it is intended to emphasize the fact fluorinated liquids, perfluorinated liquids, and mixes of fluorinated and perfluorinated liquids can be used.

"Fluoropolymers" as used herein refer to chemical compositions comprised of, consisting essentially of, or consisting of polymers having a hydrocarbon moiety (e.g., an alkyl group), in which one or more hydrogen atoms bound to a carbon atom have been replaced by a fluorine atom. Fluoropolymers include perfluoropolymers in which each hydrogen atom has been replaced by a fluorine atom. The term "fluoropolymer" is understood to include compositions comprising one or more fluoropolymers and/or perfluoropolymers unless stated otherwise.

Where both fluoropolymers and perfluoropolymers are both used (e.g., fluoropolymers and/or perfluoropolymers), it is intended to emphasize the fact that fluoropolymers, perfluoropolymers, and mixes of fluoropolymers and perfluoropolymers can be used.

Fluoropolymers and Forming Medical Devices

A diverse group of perfluoropolymers and/or fluoropolymers may be utilized to prepare the medical devices, or components thereof, described herein.

Among the perfluoropolymers that may be employed are: perfluoroalkoxy alkanes (PFA or PFAs when plural); polytetrafluoroethylene (PTFE); fluorinated ethylene propylene (FEP); expanded polytetrafluoroethylene (ePTFE or EPTFE); expanded fluorinated ethylene propylene (eFEP or EFEP); perfluoromethylvinylether (PMVE); perfluoro elastomers (e.g., FFKM, which are copolymers of tetrafluoroethylene and a perfluorinated ether such as PMVE sold under the tradename TECNOFLON® or TECNOFLON® PFR and branded as KALREZ®, CHEMRAZ® and PERLAST®) and combinations thereof. The fluoropolymers that may be employed include, but are not limited to, ethylene tetrafluoroethylene (ETFE); polyvinylidene fluoride (PVDF); fluoroelastomers (FKM and FEPM, sold under the tradenames VITON®, TECNOFLON®); vinylidene fluoride-hexafluoropropylene fluoroelastomer (VF2/HFP); vinylidene fluoride-hexafluoropropylene/tetrafluoro ethylene/hexafluoropropylene fluoroelastomer (VF2/tetrafluoro ethylene/HFP) terpolymer; and combinations thereof.

Medical devices, or portions thereof, may be produced from the above-mentioned fluoropolymers/perfluoropolymers by any process known in the art including, but not limited to, extrusion, co-extrusion, injection molding, compression molding, melt spinning, electrospinning, dip coating, chemical vapor deposition, blowing, foaming, and combinations thereof.

Fluorinated and/or Perfluorinated Liquids

Following production, and prior to use in a medical procedure, the medical device or a portion thereof comprising a perfluoropolymer and/or fluoropolymer is contacted with a fluorinated and/or perfluorinated liquid. The fluorinated liquid may include, but is not limited to, one or more fluorinated liquids selected from: perfluoropropane, perfluorobutane, perfluoropentane, perfluorohexane, perfluorooctane, perfluorodecalin, perfluoroperhydrophenanthrene, perfluorooctylbromide, perfluoro tributyl amine, perfluorotripentyl amine, poly(hexafluoropropylene oxide) and combinations thereof.

In an embodiment, the medical device comprises at least one component that comprises one or more perfluoropolymers and/or fluoropolymers coated (e.g., lubricated) with one or more fluorinated and/or perfluorinated liquids (e.g., perfluoropolymer lubricated with perfluorinated liquid(s)). In such an embodiment, the medical device comprises at least one component that comprises one or more perfluoropolymers coated (e.g., lubricated) with one or more perfluorinated liquids. In one such embodiment, the medical device comprises at least one component that comprises one or more perfluoropolymers coated (e.g., lubricated) with one or more fluorinated liquids. In another such embodiment, the medical device comprises at least one component that comprises one or more fluoropolymers coated (e.g., lubricated) with one or more perfluorinated liquids. In another such embodiment, the medical device comprises at least one component that comprises one or more fluoropolymers coated (e.g., lubricated) with one or more fluorinated liquids.

In an embodiment, the fluorinated and/or perfluorinated liquid used to treat (e.g., coat or lubricate) all or part of the one or more perfluoropolymer and/or fluoropolymer components of the medical device described herein comprises, consists essentially of, or consists of greater than:
  (i) 50%, 60%, 70%, 80%, 90%, 95%, or 98% of one or two fluorinated and/or perfluorinated compounds on a weight basis;
  (ii) 50%, 60%, 70%, 80%, 90%, 95%, or 98% fluorinated compounds on a weight basis;
  (iii) 50%, 60%, 70%, 80%, 90%, 95%, or 98% perfluorinated compounds on a weight basis; or
  (iv) 50%, 60%, 70%, 80%, 90%, 95%, or 98% fluorinated and/or perfluorinated compounds on a weight basis.

In an embodiment, the molar ratio of fluorine to hydrogen atoms present in the fluorinated and/or perfluorinated liquids used to treat (e.g., coat or lubricate) all or part of the one or more perfluoropolymer and/or fluoropolymer components of the medical device described herein is greater than 8.5:1, 9.0:1, 9.5:1, 9.7:1, 10:1, 15:1, 20:1, 30:1, 40:1, 50:1, 75:1, 90:1, 100:1, or 200:1 fluorine atoms:hydrogen atoms.

Properties of the Medical Devices

Once formed, the perfluoropolymer and/or fluoropolymer surfaces of a medical device that have been treated (e.g., coated or lubricated) with fluorinated and/or perfluorinated liquid(s) (e.g., perfluoropolymer lubricated with perfluorinated liquid(s)) resist the formation, growth, or attachment of biofilms; formation or attachment of clotted blood; and/or thrombi formation induced when exposing the surface of the medical device to blood (e.g., mammalian blood such as human, porcine, ovine, bovine, canine, feline, equine, etc.).

In an embodiment, the medical device surfaces prepared from a perfluoropolymer and/or fluoropolymer and treated with fluorinated and/or perfluorinated liquids resist the growth and attachment of bacteria. The surfaces may be resistant to the growth and attachment of bacteria including, but not limited to, *Actinobacillus, Acinetobacter* (e.g., *Acinetobacter baumannii*), *Aeromonas, Bordetella, Brevibacillus, Brucella, Bacteroides, Burkholderia, Borrelia, Bacillus, Campylobacter,* Capnocytophaga, Cardiobacterium, *Citrobacter, Clostridium, Chlamydia, Eikenella, Enterobacter, Escherichia, Francisella, Fusobacterium, Flavobacterium, Haemophilus, Helicobacter, Kingella, Klebsiella, Legionella, Listeria, Leptospirae, Moraxella, Morganella, Mycoplasma, Mycobacterium, Neisseria, Pasteurella, Proteus, Prevotella, Plesiomonas, Pseudomonas, Providencia, Rickettsia, Stenotrophomonas, Staphylococcus, Streptococcus* (group A), *Streptococcus agalactiae* (group B), *Streptococcus bovis, Streptococcus pneumoniae, Streptomyces, Salmonella, Serratia, Shigella, Spirillum, Treponema, Veillonella, Vibrio, Yersinia, Xanthomonas*, and combinations thereof.

In an embodiment, the medical device surfaces prepared from a perfluoropolymer and/or fluoropolymer and treated with fluorinated and/or perfluorinated liquids resist the formation, growth, and attachment of fungi including, but not limited to, *Aspergillus, Blastomyces dermatitidis, Candida, Coccidioides immitis, Cryptococcus, Histoplasma capsulatum* var. *capsulatum, Histoplasma capsulatum* var. *duboisii, Paracoccidioides brasiliensis, Sporothrix schenckii, Absidia corymbifera; Rhizomucor pusillus, Rhizopus* arrhizous, and combinations thereof.

In an embodiment, the medical device surfaces prepared from a perfluoropolymer and/or fluoropolymer and treated with fluorinated and/or perfluorinated liquids resist the formation, growth, and attachment of viruses including, but not limited to, cytomegalovirus (CMV), dengue, Epstein-Barr, Hantavirus, human T-cell lymphotropic virus (HTLV I/II), Parvovirus, hepatitis, human papillomavirus (HPV), human immunodeficiency virus (HIV), acquired immunodeficiency syndrome (AIDS), respiratory syncytial virus (RSV), Varicella zoster, West Nile, herpes, polio, smallpox, yellow fever, rhinovirus, coronavirus, Orthomyxoviridae (influenza viruses), and combinations thereof.

The amount of bacteria, fungi and/or viruses associated with a surface may be measured by any means known in the art, including the total mass (e.g., the mass of bacteria or fungi), and counts of the bacteria, fungi or virus dissociated from or attached to a surface followed by counting under a microscope/electron microscope or by automated means, either of which may utilize specific labels to aid in the process. The amount/number of culturable bacteria, fungi and/or viruses bound to the surface also may be determined by growing colonies or plaques. Where the bacteria or fungi form biofilms on the medical device, the percentage of the surface area covered by the biofilm also may be used as a measure of resistance to bacterial and fungal growth and/or attachment.

Figure 1:
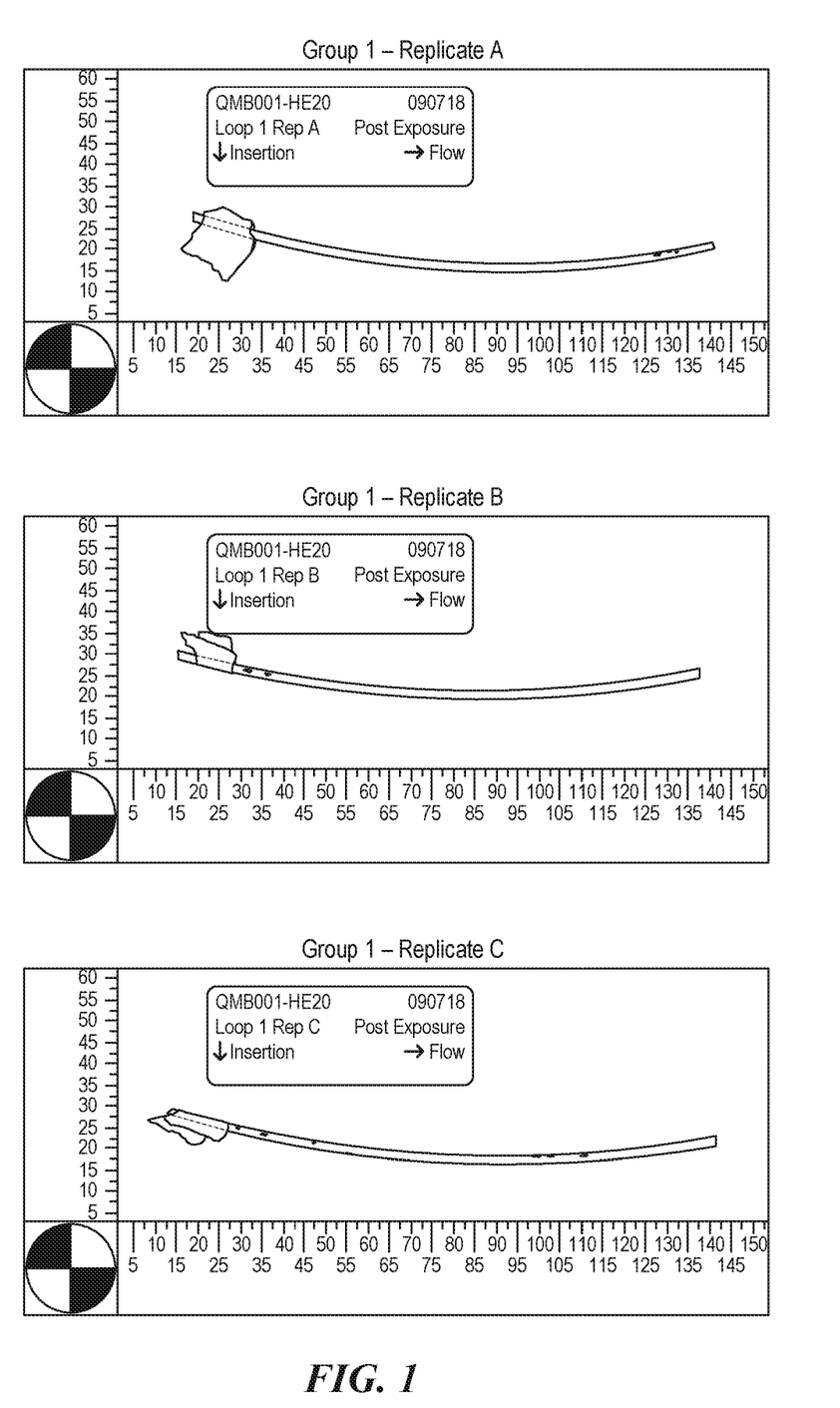
FIG. 1 provides images of catheter and PICC line samples treated as in Example 1.

In an embodiment, the perfluoropolymer and/or fluoropolymer when lubricated with fluorinated and/or perfluorinated liquid(s) (e.g., perfluoropolymer lubricated with perfluorinated liquid(s)) is non-thrombogenic or has a reduced thrombogenicity relative to the same perfluoropolymer and/or fluoropolymer that is untreated with fluorinated and/or perfluorinated liquids. In such an embodiment, the surface of the medical device resists the formation and/or attachment of blood clots relative to the surface of the same component of the medical device prepared from the perfluoropolymer and/or fluoropolymer that has not been treated with the fluorinated and/or perfluorinated liquid(s). This may be seen in FIG. 1 comparing the catheters prepared with FEP that are treated and untreated with perfluoro decalin.

The thrombogenicity (formation or attachment of clotted blood) and/or thrombi formation associated with the perfluoropolymer and/or fluoropolymer when lubricated with fluorinated and/or perfluorinated liquid(s) (e.g., perfluoropolymer lubricated with perfluorinated liquid(s)) may be determined by any suitable method known in the art. In an embodiment, the amount of clotted blood attached to a surface may be determined by measurement of a blood specific component, such as a protein or portion of a protein, that has attached to the surface. In an embodiment, the protein may be hemoglobin. In another embodiment the protein may be fibrin (as opposed to its soluble form, fibrinogen). In another embodiment, the heme (porphyrin) group of hemoglobin may be measured (e.g., following proteolytic digestion of the adherent clot with trypsin).

In an embodiment, the fluoropolymer and/or perfluorinated polymer that comprises a layer of fluorinated and/or perfluorinated liquid resists the formation, growth, and attachment of biofilms and formation of clots and/or thrombi induced when exposing the surface of a medical device to mammalian blood. The resistance may be independent of the roughness of the perfluoropolymer and/or fluoropolymer surface (measured in the absence of any liquid), particularly where the surface is completely covered by fluorinated and/or perfluorinated liquids.

In an embodiment, at least a portion of a surface of the one or more components comprised of a fluoropolymer and/or perfluorinated polymer that comprises a layer of fluorinated and/or perfluorinated liquid has a roughness as defined by the ratio of the actual surface area divided by the projected surface area that is less than 1.01, 1.05, 1.1, 1.15, 1.25, 1.35 or 1.50, wherein the roughness is determined in the absence of the fluorinated and/or perfluorinated liquid. In such an embodiment, greater than 50%, 60%, 70%, 80%, 90%, or 95% of a surface of the one or more components comprised of a fluoropolymer and/or perfluorinated polymer that comprises a layer of fluorinated and/or perfluorinated liquid may have a roughness as defined by the ratio of the actual surface area divided by the projected surface area that is less than 1.01, 1.05, 1.1, 1.15, 1.25, 1.35 or 1.5, wherein the roughness is determined in the absence of the fluorinated and/or perfluorinated liquid.

In an embodiment, at least a portion of a surface of the one or more components comprised of a fluoropolymer and/or perfluorinated polymer that comprises a layer of fluorinated and/or perfluorinated liquid has a roughness as defined by the ratio of the actual surface area divided by the projected surface area that is greater than 1.00, 1.01, 1.05, 1.1, 1.15, 1.25, 1.35 or 1.50, wherein the roughness is determined in the absence of the fluorinated and/or perfluorinated liquid. In such an embodiment, greater than 50%, 60%, 70%, 80%, 90%, or 95% of a surface of the one or more components comprised of a fluoropolymer and/or perfluorinated polymer that comprises a layer of fluorinated and/or perfluorinated liquid may have a roughness as defined by the ratio of the actual surface area divided by the projected surface area that is greater than 1.00, 1.01, 1.05, 1.10, or 1.15, wherein the roughness is determined in the absence of the fluorinated and/or perfluorinated liquid.

In an embodiment, at least a portion of a surface of the one or more components comprised of a fluoropolymer and/or perfluorinated polymer that comprises a layer of fluorinated and/or perfluorinated liquid has a roughness as defined by the ratio of the actual surface area divided by the projected surface area that is in a range selected from 1.00 to 1.01, 1.01 to 1.05, 1.05 to 1.10, 1.10 to 1.15, 1.15 to 1.25, 1.25 to 1.35, or 1.35 to 1.50, wherein the roughness is determined in the absence of the fluorinated and/or perfluorinated liquid. In such an embodiment, greater than 50%, 60%, 70%, 80%, 90%, or 95% of a surface of the one or more components comprised of a fluoropolymer and/or perfluorinated polymer that comprises a layer of fluorinated and/or perfluorinated liquid may have a roughness as defined by the ratio of the actual surface area divided by the projected surface area that is in a range selected from 1.00 to 1.01, 1.01 to 1.05, 1.05 to 1.10, 1.10 to 1.15, or 1.15 to 1.50, wherein the roughness is determined in the absence of the fluorinated and/or perfluorinated liquid.

Certain Embodiments

1. A medical device comprising:
    one or more components comprised of one or more fluoropolymers and/or perfluorinated polymers and a liquid comprised of one or more fluorinated and/or perfluorinated liquids;
    wherein at least a portion of a surface of the one or more components comprised of a fluoropolymer and/or perfluorinated polymer comprises a surface layer of the fluorinated and/or perfluorinated liquid.
2. The medical device of embodiment 1, wherein the fluoropolymer and/or perfluorinated polymer are present as a coating covering at least a portion of a surface of the one or more components.
3. The medical device of embodiment 1 or embodiment 2, wherein the fluoropolymer and/or perfluoropolymer comprise one or more of: PFA, PTFE, FEP, ePTFE, eFEP, ETFE, PVDF, VF2/HFP, VF2/tetrafluoro ethylene/HFP terpolymer, fluoroelastomers and/or perfluoroelastomers.
4. The medical device of any of embodiments 1 to 3, wherein the fluoropolymer and/or perfluoropolymer comprise one or more of PFA, PTFE, FEP, ePTFE, eFEP, or ETFE.
5. The medical device of any of embodiments 1 to 3, wherein the fluoropolymer and/or perfluoropolymer comprise one or more of: PVDF, VF2/HFP, VF2/tetrafluoro ethylene/HFP terpolymer, fluoroelastomers and/or perfluoroelastomers.
6. The medical device of any of embodiments 1 to 5 wherein at least a portion of a surface of the one or more components comprised of a fluoropolymer and/or perfluorinated polymer is coated with a liquid comprising one or more fluorinated and/or perfluorinated liquid.
7. The medical device of any of embodiments 1 to 6, wherein an exterior surface comprising at least one of the one or more components comprised of a fluoropolymer and/or perfluorinated polymer is coated with a liquid comprising one or more fluorinated and/or perfluorinated liquids.
8. The medical device of any of embodiments 1 to 7, wherein greater than 50%, 75%, 80%, 90%, or 100%, of an exterior surface of at least one of the one or more components comprised of a fluoropolymer and/or perfluorinated polymer is coated with a liquid comprising one or more fluorinated and/or perfluorinated liquids.
9. The medical device of any of embodiments 1 to 8, wherein the liquid comprised of one or more fluorinated and/or perfluorinated liquids comprises, consists essentially of, or consists of one or more perfluorinated liquids.
10. The medical device of any of embodiments 1 to 8, wherein the liquid comprised of one or more fluorinated and/or perfluorinated liquid comprises greater than:
    (i) 50%, 60%, 70%, 80%, 90%, 95%, or 98% of one or two fluorinated and/or perfluorinated compounds on a weight basis;
    (ii) 50%, 60%, 70%, 80%, 90%, 95%, or 98% of fluorinated compounds on a weight basis;

(iii) 50%, 60%, 70%, 80%, 90%, 95%, or 98% of perfluorinated compounds on a weight basis; or (iv) 50%, 60%, 70%, 80%, 90%, 95%, or 98% of fluorinated and/or perfluorinated compounds on a weight basis.

11. The medical device of any of embodiments 1 to 10, wherein the one or more fluorinated and/or perfluorinated liquids comprises: perfluoropropane, perfluorobutane, perfluoropentane, perfluorohexane, perfluorooctane, perfluorodecalin, perfluoroperhydrophenanthrene, perfluorooctylbromide, perfluoro tributyl amine, perfluorotripentyl amine, poly(hexafluoropropylene oxide, and combinations thereof.

12. The medical device of any of embodiments 1 to 11, wherein at least a portion of a surface of the one or more components comprised of a fluoropolymer and/or perfluorinated polymer that comprises a layer of fluorinated and/or perfluorinated liquid has a roughness as defined by the ratio of the actual surface area divided by the projected surface area that is less than 1.01, 1.05, 1.1, 1.15 or 1.5;
wherein the roughness is determined in the absence of the fluorinated and/or perfluorinated liquid.

13. The medical device of embodiment 12, wherein greater than 50%, 60%, 70%, 80%, 90%, or 95% of a surface of the one or more components comprised of a fluoropolymer and/or perfluorinated polymer that comprises a layer of fluorinated and/or perfluorinated liquid has a roughness as defined by the ratio of the actual surface area divided by the projected surface area that is less than 1.01, 1.05, 1.1, or 1.15;
wherein the roughness is determined in the absence of the fluorinated and/or perfluorinated liquid.

14. The medical device of any of embodiments 1 to 11, wherein at least a portion of a surface of the one or more components comprised of a fluoropolymer and/or perfluorinated polymer that comprises a layer of fluorinated and/or perfluorinated liquid has a roughness as defined by the ratio of the actual surface area divided by the projected surface area that is greater than 1.01, 1.05, 1.1, or 1.15; and which may be less than 1.5;
wherein the roughness is determined in the absence of the fluorinated and/or perfluorinated liquid.

15. The medical device of embodiment 14, wherein greater than 50%, 60%, 70%, 80%, 90%, or 95% of a surface of the one or more components comprised of a fluoropolymer and/or perfluorinated polymer that comprises a layer of fluorinated and/or perfluorinated liquid has a roughness as defined by the ratio of the actual surface area divided by the projected surface area that is greater than 1.00, 1.01, 1.05, 1.1, or 1.15;
wherein the roughness is determined in the absence of the fluorinated and/or perfluorinated liquid.

16. The medical device of any of embodiments 1 to 11, wherein at least a portion of a surface of the one or more components comprised of a fluoropolymer and/or perfluorinated polymer that comprises a layer of fluorinated and/or perfluorinated liquid has a roughness as defined by the ratio of the actual surface area divided by the projected surface area that is in a range selected from 1.00 to 1.01, 1.01 to 1.05, 1.05 to 1.10, 1.10 to 1.15, or 1.15 to 1.5; wherein the roughness is determined in the absence of the fluorinated and/or perfluorinated liquid.

17. The medical device of embodiment 16, wherein greater than 50%, 60%, 70%, 80%, 90%, or 95% of a surface of the one or more components comprised of a fluoropolymer and/or perfluorinated polymer that comprises a layer of fluorinated and/or perfluorinated liquid may have a roughness as defined by the ratio of the actual surface area divided by the projected surface area that is in a range selected from 1.00 to 1.01, 1.01 to 1.05, 1.05 to 1.10, 1.10 to 1.15, or 1.15 to 1.5; wherein the roughness is determined in the absence of the fluorinated and/or perfluorinated liquid.

18. The medical device of any of embodiments 1 to 17, wherein the device is selected from the group consisting of: catheters, tubing, shunts, grafts, stents, extracorporeal circuits including extracorporeal membrane oxygenation circuits, implanted devices, medical testing devices, cell culture bags, blood bags and artificial organs.

19. A method of making a medical device according to any of embodiments 1 to 18, wherein the one or more components is prepared by a method comprising one or more of: machining away excess material, extrusion, co-extrusion, injection molding, compression molding, melt spinning, electrospinning, dip coating, blowing, foaming, and chemical vapor deposition.

20. The method of embodiment 19, wherein the fluoropolymer and/or perfluorinated polymer are present as a coating on at least a portion of a surface of the one or more components, the method comprising: applying the fluoropolymer and/or perfluoropolymer by a method selected from the group consisting of: extrusion, co-extrusion, injection molding, compression molding, melt spinning, electrospinning, dip coating, blowing, foaming, and/or chemical vapor deposition.

21. A method of treatment comprising contacting mammalian blood, mammalian plasma, mammalian cerebrospinal fluid, mammalian serum, and/or a mammalian body or part thereof with a medical device according to any of embodiments 1 to 18.

22. The method of embodiment 21, wherein the medical device is contacted with blood.

23. The method of embodiment 22, wherein the blood is not heparinized or contains less than 1, 0.5, or 0.25 Howell units of heparin per ml.

24. The method of embodiment 21, wherein the medical device is contacted with a human body part.

25. The method of any of embodiments 21 to 24 wherein the device is selected from the group consisting of: catheters, tubing, shunts, grafts, stents, extracorporeal circuits including extracorporeal membrane oxygenation circuits, implanted devices, medical testing devices, cell culture bags, blood bags and artificial organs.

26. The method of treatment according to any of embodiments 21 to 25, wherein the body or part is that of a human subject or patient.

27. The method of treatment according to any of embodiments 21 to 25, wherein the treatment is conducted ex vivo or in vitro.

EXAMPLES

Example 1

Three catheters made from FEP, a thermal set polyurethane PICC line and a silicone catheter were obtained. Samples were, as indicated, treated with a fluorinated or perfluorinated liquid.

A sample of blood was drawn from a sheep, treated with 1 Howell unit of heparin per ml, and subsequent studies utilizing the heparinized blood were initiated within 30 minutes of the blood draw. The Activated Clotting Time (ACT) was between 150 and 250 seconds.

A test loop was prepared from 140 cm of tubing from a LivaNova® perfusion pack and filled with sheep blood heparinized as described above. Lengths of the catheters and PICC lines (between 10-15 cm) were inserted into the test loop using peel-away introducers. Each test group (type of catheter or PICC line and treatment) consisted of three replicates. For each test group a test loop was prepared and the catheter or PICC lines were inserted into the loop in the same direction with at least 5 cm between the insertion site of one device and the tip of the next device. Blood was circulated through the loop at 37±1° C. for 4 hours±30 minutes.

At the end of the 4-hour period the catheter and PICC line samples were removed, washed gently with normal saline so as not to remove blood that had clotted and attached to the samples, and the samples were photographed. Samples were scored on a scale of 1-5 as indicated in Table 1.

TABLE 1

| Thrombus Formation Score | Score Criterion | Thrombogenicity Evaluation |
| --- | --- | --- |
| 0 | Minimal to nonexistent thrombus formation (1% or less) | Thromboresistant |
| 1 | Minimal - Thrombus observed to be covering 2 to 10% of material length/area | |
| 2 | Mild - Thrombus observed to be covering 11 to 25% of material length/area | |
| 3 | Moderate - Thrombus observed to be covering 26 to 50% of material length/area | Suspected Thrombogenic (further evaluation recommended) |
| 4 | Extensive - Thrombus observed to be covering 51 to 75% of material length/area | Thrombogenic |
| 5 | Severe - Thrombus observed to be covering >75% of material length/area | |

Note:
Any thrombus formation associated with the insertion site for the articles should be noted and digital images prepared but is excluded from the scoring determination. This test is determining material mediated adherent thrombus formation, therefore only thrombus observed that is adhered to the article is used to determine the score.

The sample groups and final results are as follows:
Group 1: FEP treated with perfluorotributylamine—Thromboresistant
Group 2: FEP untreated—Thrombogenic
Group 3: Thermoset polyurethane PICC line untreated—Suspected Thrombogenic
Group 4: FEP treated with perfluorodecalin—Thromboresistant

The invention claimed is:
1. A medical device comprising:
one or more components comprised of one or more perfluorinated polymers and a liquid comprised of one or more perfluorinated liquids;
wherein at least a portion of a surface of the one or more components comprised of the one or more perfluorinated polymers comprises a surface layer of the one or more perfluorinated liquids;
wherein greater than 50% of a surface of the one or more components comprised of the one or more perfluorinated polymers that comprises a layer of the one or more perfluorinated liquids has a roughness as defined by a ratio of an actual surface area divided by a projected surface area that is greater than 1.00; wherein the roughness is determined in the absence of the one or more perfluorinated liquids;
wherein the one or more perfluorinated polymers comprises fluorinated ethylene propylene (FEP), polytetrafluoroethylene (PTFE), or a combination thereof; and
wherein the one or more perfluorinated liquids comprises perfluorodecalin, perfluorotributylamine or a combination thereof.

2. The medical device of claim 1, wherein the one or more perfluorinated polymers are present as a coating covering at least a portion of a surface of the one or more components.

3. The medical device of claim 1, wherein the one or more perfluorinated polymers comprises PTFE.

4. The medical device of claim 1, wherein at least a portion of a surface of the one or more components comprised of the one or more perfluorinated polymers are coated with the liquid comprising the one or more perfluorinated liquids.

5. The medical device of claim 1, wherein an exterior surface comprising at least one of the one or more components comprised of the one or more perfluorinated polymers is coated with the liquid comprising the one or more perfluorinated liquids.

6. The medical device of claim 5, wherein greater than 50% of the exterior surface of at least one of the one or more components comprised of the one or more perfluorinated polymers is coated with the liquid comprising the one or more perfluorinated liquids.

7. The medical device of claim 1, wherein the liquid comprised of the one or more perfluorinated liquids comprises greater than:
(i) 95% of one or two perfluorinated compounds on a weight basis; or
(ii) 95% of perfluorinated compounds on a weight basis.

8. The medical device of claim 1, wherein the one or more perfluorinated liquids comprises: perfluorodecalin.

9. The medical device of claim 1, wherein at least a portion of a surface of the one or more components comprised of the one or more perfluorinated polymers that comprises the layer of the one or more perfluorinated liquids has a roughness as defined by the ratio of the actual surface area divided by the projected surface area that is less than 1.5;
wherein the roughness is determined in the absence of the one or more perfluorinated liquids.

10. The medical device of claim 9, wherein greater than 50% of a surface of the one or more components comprised of the one or more perfluorinated polymers that comprises the layer of the one or more perfluorinated liquids has a roughness as defined by the ratio of the actual surface area divided by the projected surface area that is less than 1.15;
wherein the roughness is determined in the absence of the one or more perfluorinated liquids.

11. The medical device of claim 1, wherein at least a portion of a surface of the one or more components comprised of the one or more perfluorinated polymers that comprises the layer of the one or more perfluorinated liquids has a roughness as defined by the ratio of the actual surface area divided by the projected surface area that is greater than 1.01;
wherein the roughness is determined in the absence of the one or more perfluorinated liquids.

12. The medical device of claim 1, wherein at least a portion of a surface of the one or more components comprised of the one or more perfluorinated polymers that comprises the layer of the one or more perfluorinated liquids has a roughness as defined by the ratio of the actual surface area divided by the projected surface area that is in a range selected from 1.01 to 1.05, 1.05 to 1.10, 1.10 to 1.15, or 1.15 to 1.50; wherein the roughness is determined in the absence of the one or more perfluorinated liquids.

13. The medical device of claim 12, wherein greater than 50% of a surface of the one or more components comprised of the one or more perfluorinated polymers that comprises the layer of the one or more perfluorinated liquids has a roughness as defined by the ratio of the actual surface area divided by the projected surface area that is in a range selected from 1.01 to 1.05, 1.05 to 1.10, or 1.10 to 1.15; wherein the roughness is determined in the absence of the one or more perfluorinated liquids.

14. The medical device of claim 1, wherein the medical device is selected from the group consisting of: catheters, tubing, shunts, grafts, stents, extracorporeal circuits including extracorporeal membrane oxygenation circuits, implanted devices, medical testing devices, cell culture bags, blood bags and artificial organs.

15. A method of making a medical device according to claim 14, wherein the one or more components is prepared by a method comprising one or more of: machining away excess material, extrusion, co-extrusion, injection molding, compression molding, melt spinning, electrospinning, dip coating, blowing, foaming, and chemical vapor deposition, and wherein the one or more perfluorinated polymers are present as a coating on at least a portion of a surface of the one or more components, the method comprising: applying the one or more perfluorinated polymers by a method selected from the group consisting of: extrusion, co-extrusion, injection molding, compression molding, melt spinning, electrospinning, dip coating, blowing, foaming, or chemical vapor deposition.

16. The medical device of claim 1, wherein the one or more perfluorinated polymers comprises fluorinated ethylene propylene (FEP).

17. The medical device of claim 1, wherein the one or more perfluorinated liquids comprises perfluorotributylamine.

18. The medical device of claim 1, wherein the one or more perfluorinated polymers comprises fluorinated ethylene propylene (FEP) and the one or more perfluorinated liquids comprises perfluorotributylamine.

19. The medical device of claim 1, wherein the one or more perfluorinated polymers comprises fluorinated ethylene propylene (FEP) and the one or more perfluorinated liquids comprises perfluorodecalin.

20. The medical device of claim 1, wherein the one or more perfluorinated polymers comprises polytetrafluoroethylene (PTFE) and the one or more perfluorinated liquids comprises perfluorotributylamine.

21. The medical device of claim 1, wherein the one or more perfluorinated polymers comprises polytetrafluoroethylene (PTFE) and the one or more perfluorinated liquids comprises perfluorodecalin.

* * * * *